United States Patent
Liu et al.

(10) Patent No.: US 7,285,698 B2
(45) Date of Patent: Oct. 23, 2007

(54) METHOD FOR MANUFACTURING ALKYLATE OIL WITH COMPOSITE IONIC LIQUID USED AS CATALYST

(75) Inventors: Zhichang Liu, Beijing (CN); Chunming Xu, Beijing (CN); Chongpin Huang, Beijing (CN)

(73) Assignee: University of Petroleum, Beijing, Beijing (CN)

( * ) Notice: Subject to any disclaimer, the term of this patent is extended or adjusted under 35 U.S.C. 154(b) by 431 days.

(21) Appl. No.: 10/704,132

(22) Filed: Nov. 10, 2003

(65) Prior Publication Data

US 2004/0133056 A1    Jul. 8, 2004

(30) Foreign Application Priority Data

Nov. 12, 2002    (CN) ................ 02 1 49296

(51) Int. Cl.
    *C07C 2/58*    (2006.01)
    *C07C 2/56*    (2006.01)
(52) U.S. Cl. ................... 585/721; 585/709
(58) Field of Classification Search ......... 585/721, 585/709; 422/189, 190, 224
    See application file for complete search history.

(56) References Cited

U.S. PATENT DOCUMENTS

| | | | | |
|---|---|---|---|---|
| 2,389,550 | A | * | 11/1945 | Ross et al. ............ 585/729 |
| 4,094,924 | A | * | 6/1978 | Siskin et al. ........... 585/721 |
| 4,301,315 | A | * | 11/1981 | Haskell et al. ......... 585/304 |
| 5,073,674 | A | * | 12/1991 | Olah .................... 585/725 |
| 5,481,057 | A | * | 1/1996 | Bell et al. ............. 585/722 |
| 5,707,923 | A | * | 1/1998 | Hutchens et al. ....... 585/701 |
| 5,731,101 | A | | 3/1998 | Sherif et al. |
| 5,824,832 | A | | 10/1998 | Sherif et al. |
| 5,994,602 | A | | 11/1999 | Abdul-Sada et al. |
| 6,235,959 | B1 | * | 5/2001 | Hirschauer et al. ..... 585/709 |

FOREIGN PATENT DOCUMENTS

| FR | 2 626 572 | 8/1989 |
|---|---|---|
| WO | WO 99/03163 | 1/1999 |
| WO | WO 00/41809 | 7/2000 |

* cited by examiner

*Primary Examiner*—Glenn Caldarola
*Assistant Examiner*—John Douglas
(74) *Attorney, Agent, or Firm*—Gary M. Nath; Tanya E. Harkins; Ari G. Zytcer (57) ABSTRACT

The present invention pertains to a method for manufacturing alkylate oil using a composite ionic liquid as catalyst. A mixture of isobutane and C4 olefins is used as the raw material, and a composite ionic liquid is used as catalyst to carry out an alkylation reaction. The alkane/olefin ratio in the raw material is higher than 1:1. In the composition of the aforementioned composite ionic liquid catalyst, the cations come from a hydrohalide of an alkyl-containing amine or pyridine, while the anions are composite coordinate anions coming from two or more metal compounds. One of the metal compounds is an aluminum compound, while other metal compounds are compounds of Group IB and Group IIB elements of the Periodic Table and the transition metals. The present invention also provides a design of static mixer reaction apparatus that can realize the aforementioned manufacturing method. The method of the present invention increases the selectivity of the alkylation reaction to give the alkylation product a relatively high octane number and further increase the product yield. Also, the manufacturing operation is simplified, and the cost can be reduced. This method is an environmentally friendly method that will not pollute the environment.

21 Claims, 2 Drawing Sheets

METHOD FOR MANUFACTURING ALKYLATE OIL WITH COMPOSITE IONIC LIQUID USED AS CATALYST

TECHNICAL FIELD

The present invention pertains to a method for manufacturing alkylate oil in the petrochemical field. In particular, the present invention pertains to a method for manufacturing alkylate oil with a composite ionic liquid used as catalyst.

BACKGROUND OF THE TECHNOLOGY

Accompanying the quick development of the automobile industry and more and more attention paid to environmental protection, the worldwide demand for leadless high-octane gasoline has increased continuously. In the meantime, the content of olefins and arenes contained in gasoline will also be limited. Under these circumstances, adding alkylate oil (agent) to gasoline is an effective method for maintaining a high octane number and low vapor pressure for gasoline.

Alkylate oil is a fuel product. It is a liquid product manufactured from C4 olefins and alkanes under catalysis of an acidic catalyst. It can be considered to be a special alkylation product. The C8 content and the TMP/DMH (trimethyl pentane/dimethyl hexane) ratio are important quality indexes of the alkylate oil product. Currently, the popular manufacturing methods used in industry include the sulfuric acid method and hydrofluoric acid method. In other words, concentrated sulfuric acid and hydrofluoric acid are used as catalysts to conduct the alkylation reaction between alkanes and olefins. However, these liquid strong acids are highly corrosive, which causes many problems, including difficult manufacturing process, complicated product post-treatment, and environmental pollution. Since protection of the human living environment has become a very important issue in the modern world, study and development of a new generation of alkylation catalyst and reaction technology, especially, the technology for manufacturing alkylate oil has become an important research subject in the petrochemical catalysis and reaction industrial field.

In recent years, most of the foreign and domestic studies on alkylation technology have focused on the study of solid acid catalysts and their manufacturing technology in order to solve the problems of pollution and equipment corrosion caused by the sulfuric acid method and hydrofluoric acid method. There have been many reports on various new solid catalysts used for the aforementioned alkylation reaction. However, they all have a common problem, that is, in spite of the excellent initial activity, the catalyst becomes deactivated quickly under normal conditions. The conversion rate of the olefin drops from 100% to a very low level within several hours or even tens of minutes. The main reason causing deactivation of the catalyst is the acid position of the solid acid catalyst. The olefins present in the raw material and the olefins or carbon cations generated during the reaction will undergo polymerization, cyclization, or other secondary reactions, generating C9-36 macromolecular olefin compounds, which not only cover the active sites of the catalyst but also block the pores of the catalyst. Consequently, an alkylation reaction system under supercritical conditions was developed by taking advantage of the excellent dissolving power of the supercritical fluid. However, most of the active sites are concentrated in the pores of the aforementioned catalyst, and the dissolving power of the supercritical fluid significantly decreases in the pores. Consequently, although the catalytic period of the catalyst can be prolonged under supercritical conditions, current research results indicate that a supercritical system is unable to completely prevent coking and deactivation of the catalyst. Also, since relatively high temperature and pressure are required for the supercritical reaction, the selectivity of the alkylation reaction decreases as the reaction time passes.

Relatively successful examples of solid acid catalysts in the aspect of alkylation include the supercritical system developed by the Chinese Academy of Petroleum Science and the akylene technology invented by UOP Co. of the USA. However, the aforementioned two technologies still have some disadvantages. For example, the supercritical reaction has relatively high requirements for equipment and also has the aforementioned problem, that is, the selectivity decreases as the reaction time passes. In the alkylene technology, the catalyst can be recycled for reuse. However, a large amount of solvent is needed in this technology. Recycling and reuse of these solvents will also bring many problems. In addition, both of the aforementioned two technologies require the establishment of a completely new set of manufacturing equipment, which leads to a large investment.

An ionic liquid is a salt existing in the form of a liquid at room temperature. It has many special properties. For example, its saturated vapor pressure is very low, close to zero. It can dissolve many organic and inorganic compounds and has no corrosivity. Ionic liquids with different acidities can be prepared by adjusting the types and quantities of the cations and anions. Currently, the research concerning preparation and application of ionic liquids is still growing, and increasingly more types of ionic liquids are being manufactured and application fields being developed.

There is also a relatively high number of patents concerning alkylation reactions conducted with ionic liquids used as catalyst or solvent. However, most of the patents pertain to the alkylation process of benzene and its derivatives with olefins. Examples of such patents include U.S. Pat. No. 5,994,602, U.S. Pat. No. 5,824,832, and WO 99/03163. French patent FR 2,626,572 uses imidazolium or quaternary amine ionic liquids as a catalyst for isoalkanes and olefins. However, the main reaction products of this patent are isomeric C6 or C7, while the content of C8 alkanes in the product is very low. It does not have practical application value for alkylate oil. Also, the imidazolium ionic liquids are not well used or popularized because of their difficult synthesis process and high price.

Both U.S. Pat. No. 5,731,101 and WO 00/41809 provide a method that can easily manufacture ionic liquids at room temperature. In other words, the hydrohalide of an alkyl-containing amine reacts with a metal halide to manufacture an ionic liquid. This product is in the form of a liquid at room temperature. Its anionic part only contains one metal. The aforementioned patents in this field also disclose applications of this type of ionic liquid as a catalyst for alkylation of benzene and olefins but has no description pertaining to the alkylation reaction between isoalkanes and olefins, that is, manufacturing of alkylate oil.

It is well known to the researcher in this field that one of the keys for manufacturing high-quality alkylate oil is to increase the selectivity of the alkylation reaction. None of the aforementioned conventional alkylation reaction methods can satisfy this demand.

The Stratoc reactor that is usually used during the process of manufacturing alkylate oil using the aforementioned industrial sulfuric acid method has a complicated configuration, the equipment is difficult to repair and maintain, and it requires a large investment. The reactor used in the hydrofluoric acid method has a relatively simple configuration. However, since it uses many types of auxiliary facilities for preventing leakage of hydrofluoric acid, the equipment and process are also complicated. In addition, both of the liquid acids are highly corrosive and have high requirements for the materials of the equipment. Also, the alkane/olefin ratio in the reactor required in the alkylation process carried out using the sulfuric acid method and the hydrofluoric acid method must reach several hundred or even a thousand in order to guarantee the high quality of the product. This requires the circulation of a large amount of isobutane, which significantly increases the operation load of the fractionating column, thus increasing the operation cost. Or, part of the product can be recycled to maintain a relatively high alkane/olefin ratio in order to reduce the amount of the recycled isobutane. This, however, increases the contact time of the alkylate oil product and the catalyst. As a result, decomposition and/or polymerization of the alkylate oil is increased, which lowers the selectivity of the alkylate oil product.

In summary, there are many disadvantages to be overcome or to improve in the current technologies for the preparation or manufacturing of alkylate oil products.

SUMMARY OF THE INVENTION

The present invention provides a method for manufacturing alkylate oil with a composite ionic liquid used as catalyst, which increases the selectivity of the alkylation reaction through the improvement of the catalyst. Compared with the conventional technology, the product of the alkylation reaction, alkylate oil, has a relatively high octane number as well as relatively high C8 content, thus further increasing the yield of the product.

According to the method of the present invention, the alkylation reaction is carried out with a mixture of isobutane and C4 olefins used as the raw material and a composite ionic liquid used as catalyst. In the raw material, the alkane/olefin ratio is higher than 1:1. In the composition of the aforementioned composite ionic liquid, the cations come from the hydrohalide of an alkyl-containing amine or pyridine, while the anions are composite coordinated anions obtained from two or more metal compounds. One of the metal compounds is an aluminum compound, while the other metal compounds are compounds of Group IB and Group IIB elements of the Periodic Table and the transition metals.

According to the method of the present invention, a composite ionic liquid is used as catalyst during the alkylation reaction, and the anionic part of the composite ionic liquid includes two or more metal compounds. The reaction product of the alkylation reaction of the present invention is the aforementioned alkylate oil. The experimental results have proved that that the obtained alkylation product has a much higher C8 content and TMP/DMH ratio than those of the conventional technology. Also, in the method of the present invention, the composite ionic liquid catalyst has good regeneration property and long-term catalytic activity and stability.

The present invention also provides an optimized method for manufacturing the composite ionic liquid catalyst.

According to the technical scheme of the present invention, this alkylation reaction can be completed in a high-pressure reactor [method] that is usually used in this field, including the continuous process and intermittent process. The present invention also provides a static mixer reactor that can realize the aforementioned alkylation reaction. This reactor includes at least one static mixer and settler, fractionating column, and other devices. The alkylation reaction is carried out in the static mixer (also acting as the reactor). The reactor can control the excess isobutane during the reaction and can circulate the composite ionic liquid catalyst during the manufacturing process. In this way, the utilization rate can be increased. Also, the equipment investment can be reduced, and the operation can be simplified.

The present invention also provides a processing method that can use the aforementioned static mixer reactor to effectively manufacture alkylate oil.

DETAILED EXPLANATION OF THE INVENTION

According to the alkylation reaction technology provided by the present invention, the alkylation reaction is carried out with a mixture of isobutane and C4 olefins used as the raw material and a composite ionic liquid used as catalyst. In the composition of the aforementioned composite ionic liquid, the cations come from the hydrohalide of an alkyl-containing amine or pyridine, while the anions are composite coordinate anions obtained from two or more compounds. One of the metal compounds is an aluminum compound, while the other metal compounds are compounds of Group IB and Group IIB elements of the Periodic Table and the transition metals.

In the method for manufacturing alkylate oil, the aforementioned composite ionic liquid is used as the catalyst. In its cationic part, the nitrogen atoms in the hydrohalide of the aforementioned alkyl-containing amine or pyridine are saturated with four substituents, among which there is at least one hydrogen atom and one alkyl group. More preferably, the aforementioned alkyl substituent is at least one selected from methyl, ethyl, propyl, butyl, amyl, and hexyl groups, such as $NEt_3H^+$, $CH_3NEt_2H^+$, etc.

As can be seen from the comparison between the present invention and the conventional technology, the cationic part of the composite ionic liquid catalyst applicable to the present invention can be basically the same. The only difference is that the composite ionic liquid used in the present invention includes two or more metal compounds. Preferably, the aluminum compound is an aluminum halide, such as aluminum trichloride, while the other metal compounds are halides, sulfates, or nitrates of copper, iron, zinc, nickel, cobalt, molybdenum, or platinum. When these metal compounds are halides, they are preferred to be chlorides or bromides, such as cuprous chloride, copper chloride, nickel chloride, copper sulfate, ferrous chloride, zinc nitrate, etc.

According to the preferable scheme of the present invention, in the anionic part, it is preferred to control the molar ratio of the aluminum compound to the other metal compounds in the range of 1:100-100:1, more preferably, in the range of 1:1-100:1, or most preferably, in the range of 5:1-50:1.

According to the method of the present invention, the raw material is basically a mixture of isobutane and C4 olefins.

Examples of C4 olefins include various normal and isometric olefins, such as 2-butylene, isobutylene, and 1-butylene, which can be used either alone or as a mixture of several. The raw material used in the actual manufacturing may contain a small amount of propylene. During manufacturing, isobutane is usually used in excess (propane, pentane, or other alkanes may also be used in a small amount). The alkane/olefin ratio in the reaction raw material should be higher than 1 and is usually in the range of 1:1-40:1 in order to achieve the purpose of increasing the selectivity of the alkylation reaction and the product yield. In the case of continuous reaction, excess isobutane can be recycled for reuse.

According to the method for manufacturing alkylate oil disclosed in the present invention, it is relatively reasonable to keep the temperature of the alkylation reaction as low as possible. However, if the temperature is too low, the operation cost will increase. Consequently, the reaction temperature can be set in the range of −20 to 100° C., preferably, in the range of 0-50° C. The end point of the reaction can be determined according to the operation of the normal alkylation reaction based on the specific situations and operation conditions of the reaction. This is very easy to those who are skilled in this field. Under general circumstances, the reaction time can be in the range of 2 sec to 60 min, preferably, in the range of 2 sec to 30 min, more preferably, in the range of 1-20 min.

The key to implementing the present invention is to use a composite ionic liquid as catalyst. It can be understood that the reaction material should be kept in the liquid state by controlling the reaction conditions during the reaction process, for example, by setting an appropriate pressure. Consequently, a certain pressure is applied during the alkylation reaction of the present invention. The lower limit of the reaction pressure should be selected appropriately so that the reaction raw material is kept in the liquid state under the reaction conditions. It can be usually set in the range of 0.1-1.6 MPa.

Based on the aforementioned description of the present invention, those who are skilled in this field can obtain specific composite ionic liquid catalysts through any feasible method. The present invention provides the following preferable preparation methods.

First preparation method: A liquid containing aluminum ions as anions is used as the raw material. In a nonoxidizing environment, the liquid is mixed with the aforementioned one or several metal compounds until the solids of the metal compound(s) disappear completely and convert into a liquid to obtain a composite ionic liquid.

The aforementioned liquid containing aluminum atoms as anions can be purchased directly on the market or prepared using the method disclosed in the current technology. For example, in a nonoxidizing environment, an aluminum compound is mixed with a hydrohalide of an alkyl-containing amine or pyridine. The mixture stirred under heating until the solids of the aluminum compound disappear completely and convert into a liquid. In this way, the ionic liquid containing aluminum metal as anions is obtained. The aluminum compound and the hydrohalide of the alkyl-containing amine or pyridine can be mixed in a molar ratio of 1:1-2.5:1.

The aforementioned reaction can be carried out in a saturated alkane solvent or without using any solvent. The saturated alkane solvent can be a C4-9 saturated alkane, such as heptane, hexane, pentane, etc. It is also possible to directly use alkylate oil as the solvent to carry out the aforementioned reaction.

The temperature of this reaction can be set in the range of 80-100° C., and the stirring reaction time is usually in the range of 1-3 h.

Second preparation method: In a nonoxidizing environment, an aluminum compound and the other one or more metal compounds are mixed with the hydrohalide of an alkyl-containing amine or pyridine. The molar ratio of the total amount of the metal compounds added to the amount of the hydrohalide added is in the range of 1:1-2.5:1. The stirred reaction is carried out at normal temperature. Liquid will be gradually generated. Stirring is continued until the solids of the metal compounds disappear completely and convert into a liquid to generate a composite ionic liquid.

It is preferred to carry out the aforementioned two methods for preparing a composite ionic liquid in a nonoxidizing environment, such as under the protection of inert gas, nitrogen, dry air, or dry gas used in a refinery plant.

The alkylation reaction of the present invention can be carried out using the normal reaction apparatus, such as an autoclave equipped with a stirring device, including batch and continuous reaction autoclaves. It is also possible to use the continuous manufacturing apparatuses that are used in the alkylation reaction carried out using sulfuric acid or hydrofluoric acid in industrial manufacturing. This can be achieved very easily by those who are skilled in this field according to the explanation of the present invention.

The present invention also provides a static mixer reaction apparatus that can use the aforementioned method of the present invention to manufacture alkylate oil continuously. This apparatus increases the efficiency of mixing the alkylation raw material and the catalyst to effectively increase the selectivity of the alkylation reaction so that the alkylation product has a relatively high octane number and the product yield is also increased. This reaction apparatus significantly simplifies the operation of the alkylation reaction, lowers the equipment investment, and increases the safety of the alkylation reaction.

The present invention also provides a process that uses the aforementioned static mixer reaction apparatus to realize the manufacturing method of the present invention of manufacturing alkylate oil.

The static mixer reaction apparatus provided by the present invention at least includes:

a static mixer where the alkylation reaction of the materials occurs, a settler used for accommodating the substance obtained after the reaction to make it deposit and separate, a fractionating device, in which the fraction at the top can be extracted and fed back into the raw material mixer.

The static mixer in the aforementioned reaction apparatus is also called a static reactor. It is possible to use a group of static mixers, which are used for premixing of the materials and the reaction, respectively. For example, the group may include the following:

a first static mixer, which is used to mix the raw materials: the mixture of isobutane and C4 olefins and part of the circulated isobutane are both fed into the first static mixer, where they are fully mixed;

a second static mixer, which is used to mix part of the circulated isobutane and the composite ionic liquid; more specifically, the supplemented composite ionic liquid, the circulated composite ionic liquid, and part of the circulated isobutane are fully mixed in the second static mixer;

a third static mixer, which is used to mix the materials coming from the first and second static mixer to carry out the alkylation reaction; more specifically, the materials coming from the first and second static mixers are simultaneously fed into the third static mixer, where they are fully mixed to carry out the alkylation reaction.

At that time, the fraction in the top of the fractioning device is fed back into the first and second static mixers. The alkylate oil can be obtained at the bottom after fractioning. More specifically, after fractionation is performed in the fractionating column, the fraction obtained in the middle upper part is isobutane, which is circulated back to the first and second static mixers. The fraction obtained in the middle part is n-butane. The fraction obtained in the middle lower part is light alkylate oil. The fraction obtained in the lower part is heavy alkylate oil.

The settler is preferred to have a material feed port and three outlets. One of the outlets is formed at the bottom and is connected to a composite ionic liquid regenerator. A flash tank can also be arranged between the settler and the fractioning device. After the substance settles and separates in the settler after the reaction, the top layer is the excess isobutane and alkylate oil. The substance in this part is fed into the flash tank, where it is flash evaporated, or directly fed into the fractionating column. The composite ionic liquid in the middle lower part is circulated into the catalyst recycling device or the second static mixer. The composite ionic liquid in the bottom part is fed into the regenerator, where it is regenerated. When a flash tank is used, the excess isobutane is circulated back into the premixer or the first and second static mixers through the top outlet of the flash tank. The reaction product mainly composed of alkylate oil and part of the isobutane are fed into the fractionating device for fractionation through the bottom outlet.

Each static mixer can be constituted with one static mixer stage or several static mixer stages which can be connected in series or in parallel to each other. Also, the mixer (such as the third static mixer) used for realizing the alkylation reaction can also be connected to a packing tower or an empty tower to form a reactor in order to maintain the continuity of the alkylation reaction.

Another purpose of the present invention is to provide a method for manufacturing alkylate oil in a static mixer reaction device using a composite alkylate oil as catalyst. This method includes the following technical scheme.

The reaction raw material and the composite ionic liquid are fed into a static mixer, where they are fully mixed to carry out alkylation reaction.

After the reaction, the substance is fed into a settler, where it settles and separates.

After the reaction product is fractionated, the alkylate oil finished product is collected.

When alkylate oil is manufactured using the aforementioned method, it is preferred to use three static mixers to carry out premixing and the alkylation reaction. A preferred process of this method may include the following steps.

As the reaction raw material, a mixture of isobutane and C4 olefins is fed together with part of the circulated isobutane into the first static mixer, where they are fully mixed (the isobutane used as the reaction raw material and the composite ionic liquid catalyst can be partially circulated). The raw material may also contain a small amount of propylene or lower alkane. The alkane/olefin ratio in the raw material is higher than 1:1 and can be in the range of 1:1-40:1. The C4 olefin is preferred to be selected from 2-butylene, isobutylene, 1-butylene, which can be used either alone or as a mixture of several.

The supplemented composite ionic liquid and part of the circulated composite ionic liquid and part of the circulated isobutane are fully mixed through the second static mixer.

The materials coming from the first and second static mixers are fed into the third static mixer, where they are fully mixed to carry out the alkylation reaction. The alkylation reaction realized in the static reactor can be carried out under normal pressure. The reaction temperature is in the range of −20 to 100° C., preferably, in the range of 0-50° C.

After the reaction, the substance settles and separates in the settler. The top layer is the excess isobutane and alkylate oil. The substance in this part is fed into the flash tank, where it is flash evaporated, or directly fed into the fractionating column. The composite ionic liquid in the middle lower part is circulated into the catalyst recycling device or the second static mixer. The composite ionic liquid in the bottom part is fed into the regenerator, where it is regenerated.

After the reaction product is fractionated in the fractionating column, the fraction obtained in the upper part is propane (when the raw material contains propylene). The fraction in the middle upper part is isobutane and is circulated back to the first and second static mixers. The fraction in the middle part is n-butane. The fraction in the middle lower part is light alkylate oil. The fraction in the lower part is heavy alkylate oil.

As described above, compared with the conventional technology, the present invention has the following remarkable features.

1) The method of the present invention uses a composite ionic liquid instead of the normal ionic liquid as catalyst, which can be used continuously for more than 48 h without losing catalytic activity. Also, the volume of the alkylate oil manufactured per pass can reach to more than 25 times the amount of the composite ionic liquid catalyst used. This means that the composite ionic liquid catalyst has a relatively long service life. The amount of the catalyst consumed per ton of alkylate oil can be kept at a very low level. This can cut the manufacturing cost.

2) The composite ionic liquid used in the method of the present invention can substantially increase the selectivity for trimethylpentane (TMP) in the C8 isoalkanes to make the alkylation product have a higher octane number and further increase the yield of the alkylation product. Since the dissolving power of the composite ionic liquid with respect to isoalkane is relatively high, this reaction can produce alkylate oil with relatively high quality at relatively low alkane/olefin ratio.

3) The composite ionic liquid used in the method of the present invention has the same low corrosivity as the normal ionic liquid, it can be separated very easily to resume its catalytic activity. No waste solvent, wastewater, or other pollutants will be generated from the manufacturing process. Consequently, the method of the present invention is also a green, environmentally friendly manufacturing process.

4) The method of the present invention has no high requirements for the material of the equipment. The composite ionic liquid used causes almost no corrosion of the equipment. Also, the composite ionic liquid is not volatile and can be separated easily from the ionic liquid. This not only can further simplify the operation and lower the equipment investment and the manufacturing cost, but can also significantly reduce the potential leakage spots during the entire process, thus making the alkylation manufacturing process safer.

5) The method of the present invention uses a static mixer reaction apparatus, in which the composite ionic liquid catalyst is fully mixed and reacted with the reaction raw material in a static mixer. The reaction raw material and the catalyst only make contact once and then pass through the reactor. There is no emulsification interface formed after the reaction. The material can settle and separate very easily in the settler and can be recycled for reuse. More specifically, the method of the present invention prevents backmixing and the occurrence of secondary reactions, such as generation of heavy alkylate oil, etc., as a result of circulated use of the raw material and the product. In this way, the quality of the alkylate oil can be improved.

6) The inspection results show that the alkylate oil produced using the method of the present invention is completely constituted of isoalkanes and has no macromolecular olefin or arene generated. The yield can reach 170-180% of the volume of the olefins used as the raw material. The percentage of C8 in the alkylate oil is usually 60-80% or higher. The most significant advantage is that the percentage of trimethylpentane in the C8 composition reaches 70% or more, and the RON octane number of the alkylate oil obtained reaches 96 or larger.

EMBODIMENT

In the following, the present invention will be explained in more detail with reference to application examples. The purpose of these application examples is to help the reader obtain a better understanding of the technical content and characteristics of the present invention. The present invention is not limited to these application examples.

I. Preparation of a Composite Ionic Liquid

APPLICATION EXAMPLE 1

0.56 mol (74.98 g) of $AlCl_3$ was slowly added to 0.282 mol (39.76 g) of triethylamine hydrochloride. n-heptane was used as solvent. Under the protection of nitrogen, the system was stirred at room temperature for 30 min. Then, the temperature was raised to 80° C., followed by 2 h of stirring until the reaction was completed, that is, until the solids disappeared completely and converted into a liquid. Upon cooling, the reaction product had divided into two phases. The upper layer was heptane, while the composition of the lower layer was the ionic liquid $[NEt_3H^+][Al_2Cl_7^-]$.

Under the protection of nitrogen, 0.056 mol (5.54 g) of CuCl was added to the synthesized ionic liquid $[NEt_3H^+][Al_2Cl_7^-]$. The temperature was raised to 100° C., followed by stirring until the CuCl reacted completely, that is, until the solids disappeared completely and converted into a liquid. In this way, a composite ionic liquid was obtained.

APPLICATION EXAMPLE 2

0.56 mol (72.6 g) of $NiCl_2$ and 0.056 mol (7.50 g) of $AlCl_3$ were slowly added to 0.282 mol (39.76 g) of triethylamine hydrochloride in dry air. The reaction was carried out under stirring. The reaction was an exothermic reaction, and a light brown liquid was obtained. The reaction temperature was held at 80° C. Then, the system was further stirred for 2 h until the reaction was completed, that is, until the solids disappeared completely and converted into a liquid. In this way, a composite ionic liquid was obtained.

APPLICATION EXAMPLE 3

0.56 mol (74.98 g) of $AlCl_3$ was slowly added to 0.282 mol (39.76 g) of triethylamine hydrochloride. Alkylate oil was used as solvent. Under the protection of nitrogen, the system was stirred at room temperature for 30 min. Then, the temperature was raised to 80° C., followed by 2 h of stirring to completely carry out the reaction. Under the protection of a mixture of inert gases, 0.056 mol (5.54 g) of CuCl and 0.056 mol (7.26 g) of $NiCl_2$ were added. Then, the temperature was raised to 100° C., followed by stirring until CuCl and $NiCl_2$ reacted completely, that is, until the solids disappeared completely and converted into a liquid. In this way, a composite ionic liquid was obtained.

APPLICATION EXAMPLE 4

An ionic liquid was prepared under the same conditions as those described in Application Example 1. The amine salt used was pyridine hydrochloride. One of the metal compounds was $AlCl_3$, while the other metal compound was $Cu(NO_3)_2$. A composite ionic liquid was obtained.

APPLICATION EXAMPLE 5

An ionic liquid was prepared under the same conditions as those described in Application Example 2. The amine salt used was trimethylamine hydrochloride. One of the metal compounds was $AlCl_3$, while the other metal compound was $CuSO_4$. A composite ionic liquid was obtained.

II. Manufacturing of Alkylate Oil by a Batch Reaction in Autoclave

Alkylate oil is an intermediate product of fuel. It is a liquid product produced from C4 olefins and alkanes under catalysis of an acidic catalyst. High C8 content and high TMP/DMH (trimethylpentane/dimethylheptane) in alkylate oil are important indexes indicating the quality of alkylate oil.

APPLICATION EXAMPLE 6

200 mL of the composite ionic liquid obtained in Application Example 1 were added to an autoclave equipped with a stirrer. Nitrogen was used to increase the pressure to 0.5 MPa, followed by vigorous stirring. 1200 mL of a mixed raw material consisting of isobutane and 2-butylene or 1-butylene or isobutylene, or a mixture of these three butylenes, was added by a high-pressure pump. The alkane/olefin ratio in the raw material was 10:1. The reaction was carried out at 10° C. for 20 min. After the end of the reaction, the unreacted isobutane was released. The reaction product was allowed to stand in a separatory funnel. The reaction product separated into two layers. The lower layer was the ionic liquid, while the upper layer was the alkylate oil. The alkylate oil was obtained after separation. The yield of the alkylate oil obtained from the reaction was 156% of the volume of the olefin used as the raw material. The olefin conversion rate was 96%. The C8 content in the alkylate oil was 54 wt %, and TMP/DMH was 4.8.

APPLICATION EXAMPLE 7

200 mL of the composite ionic liquid obtained in Application Example 1 were added to an autoclave equipped with a stirrer. Nitrogen was used to increase the pressure to 0.5 MPa, followed by vigorous stirring. 1200 mL of a mixed raw material consisting of isobutane and butylenes (including 2-butylene, 1-butylene, and isobutylene) was added by a high-pressure pump. The alkane/olefin ratio in the raw material was 20:1. The reaction was carried out at 0° C. for 20 min. After the end of the reaction, the unreacted isobutane was released. The reaction product was allowed to stand in a separatory funnel. The reaction product separated into two layers. The lower layer was the ionic liquid, while the upper layer was the alkylate oil. The alkylate oil was obtained after separation. The yield of the alkylate oil obtained from the reaction was 168% of the volume of the olefin used as the raw material. The olefin conversion rate was 98%. The C8 content in the alkylate oil was 49 wt %, and TMP/DMH was 5.2.

APPLICATION EXAMPLE 8

200 mL of the composite ionic liquid obtained in Application Example 2 were added to an autoclave equipped with a stirrer. Nitrogen was used to increase the pressure to 0.8 MPa, followed by vigorous stirring. 400 mL of a mixed raw material consisting of isobutane and butylenes (including 2-butylene, 1-butylene, and isobutylene) was added by a high-pressure pump. The alkane/olefin ratio in the raw material was 20:1. The reaction was carried out at 25° C. for 20 min. After the end of the reaction, the unreacted isobutane was released. The reaction product was allowed to stand in a separatory funnel. The reaction product separated into two layers. The lower layer was the ionic liquid, while the upper layer was the alkylate oil. The alkylate oil was obtained after separation. The yield of the alkylate oil obtained from the reaction was 176% of the volume of the olefin used as the raw material. The olefin conversion rate was 99%. The C8 content in the alkylate oil was 61 wt %, and TMP/DMH was 4.9.

APPLICATION EXAMPLE 9

200 mL of the composite ionic liquid obtained in Application Example 3 were added to an autoclave equipped with a stirrer. Nitrogen was used to increase the pressure to 1.5 MPa, followed by vigorous stirring. 200 mL of a mixed raw material consisting of isobutane and butylenes (including 2-butylene, 1-butylene, and isobutylene) was added by a high-pressure pump. The alkane/olefin ratio in the raw material was 20:1. The reaction was carried out at 65° C. for 15 min. After the end of the reaction, the unreacted isobutane was released. The reaction product was allowed to stand in a separatory funnel. The reaction product separated into two layers. The lower layer was the ionic liquid, while the upper layer was the alkylate oil. The alkylate oil was obtained after separation. The yield of the alkylate oil obtained from the reaction was 170% of the volume of the olefin used as the raw material. The olefin conversion rate was 98%. The C8 content in the alkylate oil was 55 wt %, and TMP/DMH was 4.9.

APPLICATION EXAMPLE 10

200 mL of the composite ionic liquid obtained in Application Example 4 were added to an autoclave equipped with a stirrer. Nitrogen was used to increase the pressure to 1.0 MPa, followed by vigorous stirring. 100 mL of a mixed raw material consisting of isobutane and butylenes (including 2-butylene, 1-butylene, and isobutylene) was added by a high-pressure pump. The alkane/olefin ratio in the raw material was 30:1. The reaction was carried out at 50° C. for 15 min. After the end of the reaction, the unreacted isobutane was released. The reaction product was allowed to stand in a separatory funnel. The reaction product separated into two layers. The lower layer was the ionic liquid, while the upper layer was the alkylate oil. The alkylate oil was obtained after separation. The yield of the alkylate oil obtained from the reaction was 164% of the volume of the olefin used as the raw material. The olefin conversion rate was 97%. The C8 content in the alkylate oil was 62 wt %, and TMP/DMH was 5.1.

III. Manufacturing of Alkylate Oil by Continuous Reaction in Autoclave

Since the density of the ionic liquid is much higher than that of the reaction raw material and the alkylate oil product, the ionic liquid is always kept in the middle lower part of the autoclave. The reaction product can be extracted continuously from the top of the autoclave. After the unreacted excess isobutane is gasified and separated, the alkylate oil product can be obtained.

APPLICATION EXAMPLE 11

200 mL of the composite ionic liquid obtained in Application Example 5 were added to an autoclave equipped with a stirrer. Nitrogen was used to increase the pressure to 0.1 MPa, followed by vigorous stirring. 1200 mL of a mixed raw material consisting of isobutane and 2-butylene or 1-butylene or isobutylene, or a mixture of these three butylenes, was added by a high-pressure pump. The alkane/olefin ratio in the raw material was 10:1. The reaction was carried out at −10° C. The mixture of the excess alkane and the alkylate oil product was discharged continuously from the top of the autoclave. After separation, the alkylate oil product was obtained. The yield of the alkylate oil obtained from the reaction was 172% of the volume of the olefin used as the raw material. The olefin conversion rate was 100%. The C8 content in the alkylate oil was 72 wt %, and TMP/DMH was 5.6.

APPLICATION EXAMPLE 12

200 mL of the composite ionic liquid obtained in Application Example 1 were added to an autoclave equipped with a stirrer. Nitrogen was used to increase the pressure to 1.6 MPa, followed by vigorous stirring. 2000 mL of a mixed raw material consisting of isobutane, 2-butylene and isobutylene was added by a high-pressure pump. The alkane/olefin ratio in the raw material was 200:1. The reaction was carried out at 80° C. The mixture of the excess alkane and the alkylate oil product was discharged continuously from the top of the autoclave. After separation, the alkylate oil product was obtained. The yield of the alkylate oil obtained from the reaction was 165% of the volume of the olefin used as the raw material. The olefin conversion rate was 99%. The C8 content in the alkylate oil was 74 wt %, and TMP/DMH was 4.3.

APPLICATION EXAMPLE 13

200 mL of the composite ionic liquid obtained in Application Example 1 were added to an autoclave equipped with a stirrer. Nitrogen was used to increase the pressure to 1.0 MPa, followed by vigorous stirring. 600 mL of a mixed raw material consisting of isobutane and 1-butylene was added by a high-pressure pump. The alkane/olefin ratio in the raw material was 100:1. The reaction was carried out at 10° C. The mixture of the excess alkane and the alkylate oil product was discharged continuously from the top of the autoclave. After separation, the alkylate oil product was obtained. The yield of the alkylate oil obtained from the reaction was 174% of the volume of the olefin used as the raw material. The olefin conversion rate was 99%. The C8 content in the alkylate oil was 78 wt %, and TMP/DMH was 6.8.

APPLICATION EXAMPLE 14

200 mL of the composite ionic liquid obtained in Application Example 1 were added to an autoclave equipped with a stirrer. Nitrogen was used to increase the pressure to 0.5 MPa, followed by vigorous stirring. 4000 mL of a mixed raw material consisting of isobutane and 2-butylene or 1-butylene or isobutylene, or a mixture of these three butylenes, was added by a high-pressure pump. The alkane/olefin ratio in the raw material was 150:1. The reaction was carried out at 0° C. The mixture of the excess alkane and the alkylate oil product was discharged continuously from the top of the autoclave. After separation, the alkylate oil product was obtained. The yield of the alkylate oil obtained from the reaction was 182% of the volume of the olefin used as the raw material. The olefin conversion rate was 99%. The C8 content in the alkylate oil was 80 wt %, and TMP/DMH was 6.9.

IV. Continuous Manufacturing of Alkylate Oil in Static Mixer Reaction Apparatus

APPLICATION EXAMPLE 15

Figure 1:
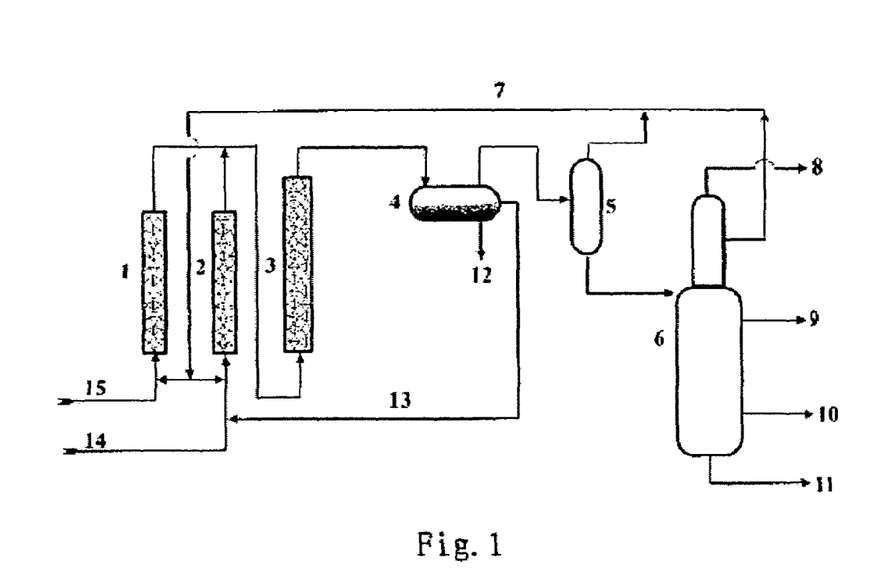
FIG. 1 is a flow chart illustrating a static mixer reaction apparatus.

The flow chart of the static mixer reaction apparatus used in the method of the present invention is shown in FIG. 1. (1) represents the first static mixer; (2) represents the second static mixer; (3) represents the third static mixer; (4) represents a settler; (5) represents a flash tank; (6) represents a fractionating column; (7) represents circulated isobutane; (8) represents propane; (9) represents n-butane; (10) represents light alkylate oil; (11) represents heavy alkylate oil; (12) represents the ionic liquid to be regenerated; (13) represents circulated ionic liquid catalyst; (14) represents the supplemented ionic liquid catalyst; and (15) represents the reaction raw material.

Reaction raw material (15) prepared by mixing isobutane and butylene at a certain ratio (2:1) with part of the circulated butane (7) was fully mixed in the first static mixer (1). Then, it was fed into the third static mixer (3) together with a mixture of the supplemented ionic liquid (14), circulated composite ionic liquid (13), and part of the circulated butane (7) that had been fully mixed in the first static mixer (1) to carry out the alkylation reaction. The reaction temperature was 30° C., the pressure was 1.0 MPa, and the total alkane/olefin ratio maintained in the reactor was 10:1. After the reaction, the substance settled and separated in settler (4). The ionic liquid (12) in the bottom layer was fed into a regenerator where it was regenerated. The ionic liquid (13) in the middle lower part was circulated back to the second static mixer (2). The excess isobutane and alkylate oil in the top layer were fed into flash tank (5), where flash evaporation was performed. The excess isobutane (7) was discharged from the top outlet of flash tank (5) and circulated back to the first static mixer (1) and the second static mixer (2). The main substances in the bottom of flash tank (5) were alkylate oil and part of the isobutane (7), which were fed into fractionating column (6) where fractionation was performed. The fraction of isobutane (7) in the middle upper part of the fractionating column was cooled off and then circulated back to the first static mixer (1) and the second static mixer (2) to guarantee a relatively low reaction temperature. The middle part of fractionating column (6) was n-butane (9). The middle lower part was light alkylate oil (10). The lower part was heavy alkylate oil (11). The yield of the alkylate oil obtained from the reaction was 176% of the volume of the olefin used as the raw material. The olefin conversion rate was 98%. The C8 content in the alkylate oil was 76 wt %, and TMP/DMH was 6.7.

APPLICATION EXAMPLE 16

Figure 2:
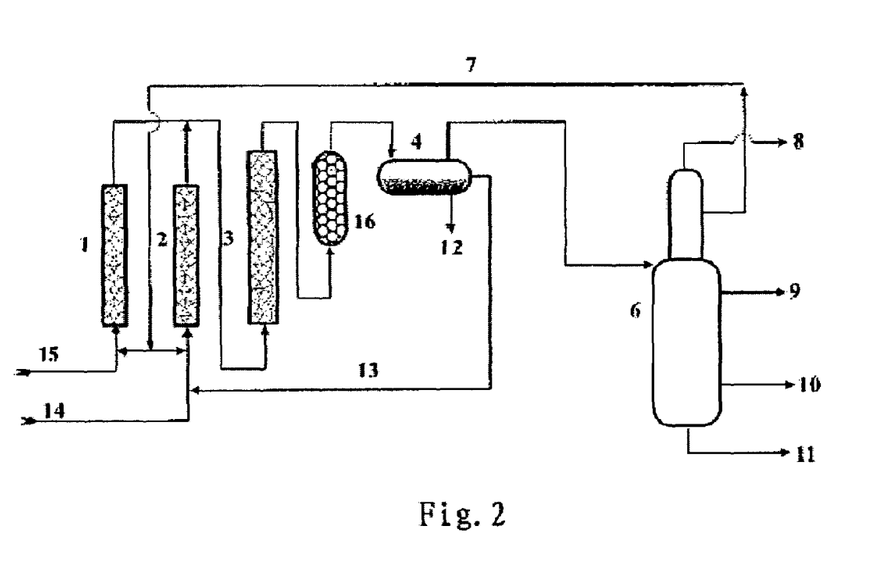
FIG. 2 is a flow chart illustrating a static mixer reaction apparatus equipped with a packing tower.

The reaction process is shown in FIG. 2. Compared with Application Example 15, a static mixer and a packing tower were combined to form a new reactor, which was equivalent to the third static mixer shown in FIG. 1. Also, flash tank (5) was not used. (16) represents the packing tower, which constitutes the reactor together with static mixer (3).

Reaction raw material (15) prepared by mixing isobutane and butylene containing a small amount of propylene at a certain ratio (5:1) with part of the circulated butane was fully mixed in the first static mixer (1). Then, it was fed into the third static mixer (3) together with a mixture of the supplemented ionic liquid (14), circulated composite ionic liquid (13), and part of the circulated butane (7) that had been fully mixed in the first static mixer (1). Then, the mixture was fed into packing tower (16) to continue the alkylation reaction. The reaction temperature was 5° C., the pressure was 0.6 MPa, and the total alkane/olefin ratio maintained in the reactor was 30:1. After the reaction, the substance settled and separated in settler (4). The ionic liquid (12) in the bottom layer was fed into a regenerator where it was regenerated. The ionic liquid (13) in the middle lower part was circulated back to the second static mixer (2). The excess isobutane (7) and alkylate oil in the top layer were fed into fractionating column (6) where fractionation was performed. The top in fractionating column (6) was propane fraction (8). The middle upper part was isobutane fraction (7), which was cooled off and then circulated back to the first static mixer (1) and the second static mixer (2) to guarantee relatively low reaction temperature. The middle part was n-butane fraction (9). The middle lower part was light alkylate oil (10). The bottom part was heavy alkylate oil (11). The yield of the alkylate oil obtained from the reaction was 182% of the volume of the olefin used as the raw material. The olefin conversion rate was 99%. The C8 content in the alkylate oil was 82 wt %, and TMP/DMH was 8.2.

APPLICATION EXAMPLE 17

Figure 3:
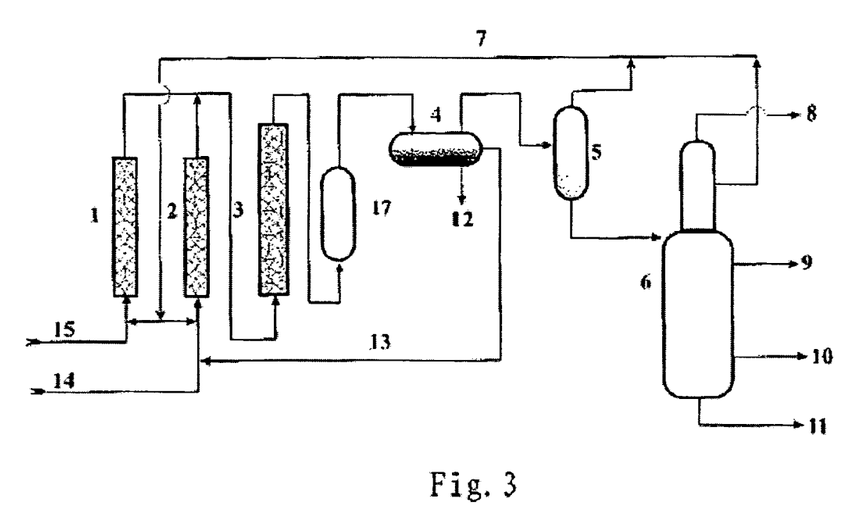
FIG. 3 is a flow chart illustrating a static mixer reaction apparatus equipped with an empty tower.

The reaction process is shown in FIG. 3. Compared with the reaction process described in Application Example 16, a flash tank was added. Also, packing tower (16) was replaced by empty tower (17). Empty tower (17) was combined with static mixer (3) to form a reactor. Reaction raw material (15) prepared by mixing isobutane and butylene at a certain ratio (1:1) with part of the circulated butane (7) was fully mixed in the first static mixer (1). Then, it was fed into the third static mixer (3) together with a mixture of the supplemented ionic liquid (14), circulated composite ionic liquid (13), and part of the circulated butane (7) that had been fully mixed in the first static mixer. Then, the mixture was fed into empty tower (17) to continue the alkylation reaction. The third static mixer (3) and empty tower (17) had a cooling device which eliminated the heat generated during the reaction. The reaction temperature was 60° C., the pressure was 1.2 MPa, and the total alkane/olefin ratio maintained in the reactor was 80:1. After the reaction, the substance settled and separated in settler (4). The ionic liquid (12) in the bottom layer was fed into a regenerator where it was regenerated. The ionic liquid (13) in the middle lower part was circulated back to the second static mixer (2). The excess isobutane and alkylate oil in the top layer were fed into flash tank (5), where flash evaporation was performed. The excess isobutane (7) was discharged from the top outlet of flash tank (5) and circulated back to the first static mixer (1) and the second static mixer (2). The main substances in the bottom part of flash tank (5) were alkylate oil and part of the isobutane (7), which were fed into fractionating column (6) where fractionation was performed. The fraction of isobutane (7) in the middle upper part of the fractionating column (6) was cooled off and then circulated back to the first static mixer (1) and the second static mixer (2) to guarantee a relatively low reaction temperature. The middle part of fractionating column (6) was n-butane (9). The middle lower part was light alkylate oil (10). The lower part was heavy alkylate oil (11). The yield of the alkylate oil obtained from the reaction was 176% of the volume of the olefin used as the raw material. The olefin conversion rate was 99%. The C8 content in the alkylate oil was 76 wt %, and TMP/DMH was 6.4.

V. Experiment for Catalytic Stability of Ionic Liquid

APPLICATION EXAMPLE 18

Under the conditions described in Application Example 13, the olefin material for reaction was supplied continuously, and the reaction product was discharged from the autoclave continuously. The olefin content in the tail gas and the composition of the alkylate oil were measured every hour. After the reaction was carried out for 48 h, no C4 olefins were detected in the tail gas. This meant that all of the olefins had been converted. The chromatography results of the alkylate oil sampled at different time intervals showed that during the 48 h of continuous reaction, the composition of the ionic liquid had no change. The C8 composition percentage was 78%. The content of trimethylpentane in the C8 composition was 74%. This application example showed that the composite ionic liquid had a relatively long period of catalytic stability.

Finally, it should be pointed out that the purpose of the aforementioned application examples is only to explain the technical scheme of the present invention and should not imply any limitation. Although the present invention has been explained in detail with reference to the preferable application examples, those who are skilled in this field should understand that any modification or equivalent substitution made to the technical scheme of the present invention but not deviating from the main point of the present invention should be covered within the scope of the claims of the present invention.

The invention claimed is:

1. A method of manufacturing alkylate oil comprising: reacting raw material in the presence of a catalyst, wherein a mixture of isobutane and C4 olefins is used as the raw material,
the raw material has an alkane/olefin ratio higher than 1:1, the catalyst is a composite ionic liquid consisting essentially of
cations coming from a hydrohalide of an alkyl-containing amine or pyridine,
anioins being composite coordinate anions coming from two or more metal compounds,
wherein at least one of the two or more metal compounds is an aluminum compound and one or more of the two or more metal compounds is a compound selected from the group consisting of Group IB elements of the Periodic Table, Group IIB elements of the Periodic Table and transition elements of the Periodic Table,
wherein the catalyst is used to carry out an alkylation reaction.

2. The method for manufacturing alkylate oil described in claim 1, wherein the nitrogen atoms in the hydrohalide of the aforementioned alkyl-containing amine or pyridine are saturated by four substituents, among which there is at least one hydrogen atom and one alkyl substituent.

3. The method for manufacturing alkylate oil as described in claim 1, wherein the aforementioned aluminum compound is a halide of aluminum, while the other metal compounds are halides, sulfates, or nitrates of copper, iron, zinc, nickel, cobalt, molybdenum, or platinum; the molar ratio of the aluminum compound to the other metal compounds is in the range of 1:100-100:1.

4. The method for manufacturing alkylate oil as described in claim 3, wherein the molar ratio of the aluminum compound to other metal compounds is in the range of 1:1-100:1.

5. The method for manufacturing alkylate oil as described in claim 2, wherein the aforementioned alkyl substituent is at least one selected from the group consisting of from methyl, ethyl, propyl, butyl, amyl, and hexyl groups.

6. The method for manufacturing alkylate oil as described in claim 2, wherein the aforementioned aluminum compound is aluminum trichloride.

7. The method for manufacturing alkylate oil as described in claim 1, wherein the C4 olefins in the raw material are selected from the group consisting of 2-butylene, isobutylene, and 1-butylene, which can be used either alone or as a mixture of several.

8. The method for manufacturing alkylate oil as described in claim 1, wherein the alkylation reaction temperature is in the range of –20 to 100° C., and pressurization is performed to control the reaction material to keep it in liquid form.

9. The method for manufacturing alkylate oil as described in claim 8, wherein the reaction pressure is in the range of 0.1-1.6 MPa, and the reaction time is in the range of about 2 sec to 30 min.

10. The method for manufacturing alkylate oil as described in claim 8, wherein the alkylation reaction temperature is in the range of 0-50° C.

11. The method for manufacturing alkylate oil as described in claim 9, wherein the alkylation reaction temperature is in the range of 0-50° C.

12. The method for manufacturing alkylate oil as described in claim 1, wherein also including preparation of a composite ionic liquid catalyst as follows: an ionic liquid containing aluminum ions as anions is used as the raw material and stirred together with the aforementioned one or more metal compounds in a nonoxidizing environment until the solids of the added metal compounds completely disappear and convert into a liquid.

13. The method for manufacturing alkylate oil as described in claim 12, wherein the aforementioned ionic liquid containing aluminum ions as anions is prepared as follows: in a nonoxidizing environment, an aluminum compound and the hydrohalide of an alkyl-containing amine or pyridine are mixed at a molar ratio of about 1:1-2.5:1 and are stirred under heating until the solids of the aluminum compound completely disappear and convert into a liquid.

14. The method for manufacturing alkylate oil as described in claim 12, wherein the reaction for preparing the ionic liquid is carried out in a saturated olefin alkane solvent or alkylate oil, the reaction temperature is in the range of about 80-100° C., and the stirring time is in the range of about 1-3 h.

15. The method for manufacturing alkylate oil as described in claim 1, wherein also including preparation of a composite ionic liquid catalyst as follows: in a nonoxidizing environment, an aluminum compound and another one or more metal compound are mixed with the hydrohalide of an alkyl-containing amine or pyridine; the molar ratio of the total amount of the metal compounds added to the amount of the hydrohalide is about 1:1-2.5:1; the mixture is stirred under normal temperature until the solids of the metal compounds completely disappear and convert into a liquid.

16. The method for manufacturing alkylate oil as described in claim 1, wherein the alkylation reaction is carried out in an autoclave and is a batch or continuous reaction process.

17. The method of manufacturing alkylate oil according to claim 1, wherein the alkylation reaction is a continuous alkylation reaction carried out using a reaction apparatus comprising a static mixer, a settler having a top outlet and a fractionating device, the method further comprising:
feeding the raw material and the composite ionic liquid into the static mixer;
fully mixing the raw material and the composite ionic liquid to carry out the alkylation reaction;
obtaining a reaction substance;
feeding the reaction substance obtained into the settler where it settles and separates;
fractionating the reaction substance to obtain a top fraction, the top fraction comprising supplemented composite ionic liquid which comprises circulated isobutene and circulated composite ionic liquid, circulated isobutene, and circulated composite ionic liquid;
circulating the top fraction back into the static mixer; and collecting alkylate oil finished product.

18. The method of manufacturing alkylate oil according to claim 17, further comprising:
providing a second static mixer, and a third static mixer to perform premixing and the alkylation reaction;
feeding the raw material together with part of the circulated isobutane into the first static mixer;
mixing the raw material and circulated isobutene;
mixing the supplemented composite ionic liquid and the circulated composite ionic liquid and part of the circulated isobutane second static mixer; and
feeding the materials coming from the first and second static mixers into the third static mixer where they are fully mixed to carry out the alkylation reaction.

19. The method for manufacturing alkylate oil as described in claim 18 wherein after the substance obtained after the reaction settles and separates, the excess isobutane and the alkylate oil in an upper part are fed into a flash tower, where flash evaporation is carried out, or directly into a fractionating tower; the composite ionic liquid in a middle lower part is circulated back to the second static mixer; and the composite ionic liquid in a lower part is fed into a regenerator, where it is regenerated.

20. The method for manufacturing alkylate oil as described in claim 19 wherein the mixture of excess isobutane and alkylate oil output from the top outlet on the settler is subjected to flash evaporation; the excess isobutane output from the top outlet of the flash tower is circulated back to the first and second static mixers; the main substances in the bottom part are alkylate oil and part of the isobutane, which are fed into a fractionating column for fractionation.

21. The method for manufacturing alkylate oil as described in claim 19 wherein after the substance is fractionated in the fractionating column, the fraction obtained in a middle upper part is isobutane, which is circulated back to the first and second static mixers; the fraction obtained in the middle lower part is light alkylate oil; and the fraction obtained in the lower part is heavy alkylate oil.

* * * * *